(12) United States Patent
Friedman et al.

(10) Patent No.: US 6,927,022 B2
(45) Date of Patent: Aug. 9, 2005

(54) HADHS AS MODIFIERS OF THE P21 PATHWAY AND METHODS OF USE

(75) Inventors: Lori Friedman, San Francisco, CA (US); Gregory D. Plowman, San Carlos, CA (US); Roel P. Funke, South San Francisco, CA (US); Marcia Belvin, Albany, CA (US); Danxi Li, San Francisco, CA (US); Stephanie A. Robertson, San Francisco, CA (US)

(73) Assignee: Exelixis, Inc., South San Francisco, CA (US)

( * ) Notice: Subject to any disclaimer, the term of this patent is extended or adjusted under 35 U.S.C. 154(b) by 0 days.

(21) Appl. No.: 10/192,353

(22) Filed: Jul. 10, 2002

(65) Prior Publication Data

US 2003/0022222 A1 Jan. 30, 2003

Related U.S. Application Data

(60) Provisional application No. 60/305,017, filed on Jul. 12, 2001, provisional application No. 60/328,491, filed on Oct. 10, 2001, and provisional application No. 60/357,452, filed on Feb. 15, 2002.

(51) Int. Cl.[7] .............................................. G01N 33/50
(52) U.S. Cl. .......................................... 435/4; 436/501
(58) Field of Search ............................... 435/4; 436/501

(56) References Cited

U.S. PATENT DOCUMENTS 5,235,033 A * 8/1993 Summerton et al. ........ 528/391
5,518,911 A * 5/1996 Abo et al.

FOREIGN PATENT DOCUMENTS

WO    WO 01/64840    * 9/2001

OTHER PUBLICATIONS

Abstract of Charreau et al (Transgene Research, 1996, vol. 5, pp. 223–234).*
Abstract of Nancarrow et al (Methods in molecular biology, 1993, vol. 18, pp. 273–303).*
Abstract of Machaty et al (Cloning Stem Cells, 202, vol. 4, pp. 21–27).*
Abstract of Hudziak et al (Antisense Nucleic Acid Drug Dev, Jun. 2000, vol. 10, pp. 163–176).*
Brenner et al (PNAS, 1998, Volt, 95, pp. 6073–6078).*
Bork, Genome Research, 2000, vol. 10, pp. 398–400.*
Brock, Biology of Microorganisms (textbook), 1979, p. 64.*
Bork and Koonin (Nature Genetics, 1998, vol. 18, pp. 313–318).*
Huynen and Bork, PNAS, 1998, vol. 95, pp. 5849–5856.*
Huynen et al, Genome Research, 2000, vol. 10, pp. 1204–1210.*
Smith, M., "Human DNA sequence from clone RP4–694B14 on chromosome 20p11.1–11.22 Contains a novel KRAB box protein with 18 C2H2 type zinc finger domains, a novel haloacid dehalogenase–like hydrolase family protein similar to (archaea) bacterial proteins, two putative novel genes, a novel pseudogene, ESTs, an STS, GSSs and three CpG islands, complete sequence." Genbank GI No. 11968366, Apr. 4, 2001.
Strausberg, R., "*Homo sapiens*, Similar to Riken cDNA 1600031M04 gene, clone MGC:26833 Image:4819016, mRNA, complete cds." Genbank GI No. 18490373, Feb. 04, 2002.
Strausberg, R., "Cloned unidirectionally; oligo–dT primed. Average insert size 2.5 kb. Library enriched for full–length clones and constructed by Life Technologies. Note: this is a NIH_MGCLibrary." Genbank GI No. 20405373, May 1, 2002.

* cited by examiner

*Primary Examiner*—Karen A. Canella
(74) *Attorney, Agent, or Firm*—Laleh Shayesteh Exelixis, Inc.

(57) ABSTRACT

Human HADH genes are identified as modulators of the p21 pathway, and thus are therapeutic targets for disorders associated with defective p21 function. Methods for identifying modulators of p21, comprising screening for agents that modulate the activity of HADH are provided.

21 Claims, No Drawings

HADHS AS MODIFIERS OF THE P21 PATHWAY AND METHODS OF USE

REFERENCE TO RELATED APPLICATIONS

This application claims priority to U.S. provisional patent application No. 60/305,017 filed Jul. 12, 2001, Ser. No. 60/328,491 filed Oct. 10, 2001, and Ser. No. 60/357,452 filed Feb. 15, 2002. The contents of the prior applications are hereby incorporated in their entirety.

BACKGROUND OF THE INVENTION

The p21/CDKN1/WAF1/CIP1 protein (El-Deiry, W. S.; et al. Cell 75: 817–825, 1993; Harper, J. W.; et al. Cell 75: 805–816, 1993; Huppi, K et al. Oncogene 9: 3017–3020, 1994) is a cell cycle control protein that inhibits cyclin-kinase activity, is tightly regulated at the transcriptional level by p53, and mediates p53 suppression of tumor cell growth. Along with p53, p21 appears to be essential for maintaining the G2 checkpoint in human cells (Bunz, F.; Dutriaux, A.; et al. Science 282:1497–1501, 1998). Sequences of p21 are well-conserved throughout evolution, and have been identified in species as diverse as human (Genbank Identifier 13643057), *Drosophila melanogaster* (GI# 1684911), *Caenorhabditis elegans* (GI#4966283), and yeast (GI#2656016).

The hydrolytic dehalogenases catalyse a nucleophilic displacement reaction, with water as the sole co-substrate. They are divided into haloalkane dehalogenases and haloacid dehalogenases (HAD). HADs belong to a large superfamily of hydrolases with diverse substrate specificity, which also includes epoxide hydrolases, phosphoglycolate phosphatases, histidinol phosphate phosphatases, nitrophenyl phosphatases and numerous putative proteins. The epoxide hydrolases (EH) add water to epoxides, forming the corresponding diol. HADH (C20orf147) is a member of the haloacid dehalogenase or epoxide hydrolase family The ability to manipulate the genomes of model organisms such as *Drosophila* provides a powerful means to analyze biochemical processes that, due to significant evolutionary conservation, have direct relevance to more complex vertebrate organisms. Due to a high level of gene and pathway conservation, the strong similarity of cellular processes, and the functional conservation of genes between these model organisms and mammals, identification of the involvement of novel genes in particular pathways and their functions in such model organisms can directly contribute to the understanding of the correlative pathways and methods of modulating them in mammals (see, for example, Mechler B M et al., 1985 EMBO J 4:1551–1557; Gateff E. 1982 Adv. Cancer Res. 37: 33–74; Watson K L., et al., 1994 J Cell Sci. 18: 19–33; Miklos G L, and Rubin G M. 1996 Cell 86:521–529; Wassarman D A, et al., 1995 Curr Opin Gen Dev 5: 44–50; and Booth D R. 1999 Cancer Metastasis Rev. 18: 261–284). For example, a genetic screen can be carried out in an invertebrate model organism having underexpression (e.g. knockout) or overexpression of a gene (referred to as a "genetic entry point") that yields a visible phenotype. Additional genes are mutated in a random or targeted manner. When a gene mutation changes the original phenotype caused by the mutation in the genetic entry point, the gene is identified as a "modifier" involved in the same or overlapping pathway as the genetic entry point. When the genetic entry point is an ortholog of a human gene implicated in a disease pathway, such as p21, modifier genes can be identified that may be attractive candidate targets for novel therapeutics.

All references cited herein, including sequence information in referenced Genbank identifier numbers and website references, are incorporated herein in their entireties.

SUMMARY OF THE INVENTION

We have discovered genes that modify the p21 pathway in *Drosophila*, and identified their human orthologs, hereinafter referred to as HADH. The invention provides methods for utilizing these p21 modifier genes and polypeptides to identify HADH-modulating agents that are candidate therapeutic agents that can be used in the treatment of disorders associated with defective or impaired p21 function and/or HADH function. Preferred HADH-modulating agents specifically bind to HADH polypeptides and restore p21 function. Other preferred HADH-modulating agents are nucleic acid modulators such as antisense oligomers and RNAi that repress HADH gene expression or product activity by, for example, binding to and inhibiting the respective nucleic acid (i.e. DNA or mRNA).

HADH modulating agents may be evaluated by any convenient in vitro or in vivo assay for molecular interaction with an HADH polypeptide or nucleic acid. In one embodiment, candidate HADH modulating agents are tested with an assay system comprising a HADH polypeptide or nucleic acid. Agents that produce a change in the activity of the assay system relative to controls are identified as candidate p21 modulating agents. The assay system may be cell-based or cell-free. HADH-modulating agents include HADH related proteins (e.g. dominant negative mutants, and biotherapeutics); HADH-specific antibodies; HADH-specific antisense oligomers and other nucleic acid modulators; and chemical agents that specifically bind to or interact with HADH or compete with HADH binding partner (e.g. by binding to an HADH binding partner). In one specific embodiment, a small molecule modulator is identified using a binding assay. In specific embodiments, the screening assay system is selected from an apoptosis assay, a cell proliferation assay, an angiogenesis assay, and a hypoxic induction assay.

In another embodiment, candidate p21 pathway modulating agents are further tested using a second assay system that detects changes in the p21 pathway, such as angiogenic, apoptotic, or cell proliferation changes produced by the originally identified candidate agent or an agent derived from the original agent. The second assay system may use cultured cells or non-human animals. In specific embodiments, the secondary assay system uses non-human animals, including animals predetermined to have a disease or disorder implicating the p21 pathway, such as an angiogenic, apoptotic, or cell proliferation disorder (e.g. cancer).

The invention further provides methods for modulating the HADH function and/or the p21 pathway in a mammalian cell by contacting the mammalian cell with an agent that specifically binds a HADH polypeptide or nucleic acid. The agent may be a small molecule modulator, a nucleic acid modulator, or an antibody and may be administered to a mammalian animal predetermined to have a pathology associated the p21 pathway.

DETAILED DESCRIPTION OF THE INVENTION

An overexpression screen was carried out in *Drosophila* to identify genes that interact with the cyclin dependent kinase inhibitor, p21 (Bourne H R, et al., Nature (1990) 348(6297):125–132; Marshall C J, Trends Genet (1991)

7(3):91–95). Expression of the p21 gene in the eye causes deterioration of normal eye morphology. The CG15771 gene was identified as a modifier of the p21 pathway. Accordingly, vertebrate orthologs of these modifiers, and preferably the human orthologs, HADH genes (i.e., nucleic acids and polypeptides) are attractive drug targets for the treatment of pathologies associated with a defective p21 signaling pathway, such as cancer.

In vitro and in vivo methods of assessing HADH function are provided herein. Modulation of the HADH or their respective binding partners is useful for understanding the association of the p21 pathway and its members in normal and disease conditions and for developing diagnostics and therapeutic modalities for p21 related pathologies. HADH-modulating agents that act by inhibiting or enhancing HADH expression, directly or indirectly, for example, by affecting an HADH function such as enzymatic (e.g., catalytic) or binding activity, can be identified using methods provided herein. HADH modulating agents are useful in diagnosis, therapy and pharmaceutical development.

Nucleic Acids and Polypeptides of the Invention

Sequences related to HADH nucleic acids and polypeptides that can be used in the invention are disclosed in Genbank (referenced by Genbank identifier (GI) number) as GI#s 11968366, 18490373 (SEQ ID NO:1), and 20405373 (SEQ ID NO:2) for nucleic acid, and GI# 4902680 (SEQ ID NO:3) polypeptides. Additionally, polypeptide sequence of SEQ ID NO:4 is a translation of SEQ ID NO:1, and can be used in the invention.

HADHs are hydrolase proteins with hydrolase domains. The term "HADH polypeptide" refers to a full-length HADH protein or a functionally active fragment or derivative thereof. A "functionally active" HADH fragment or derivative exhibits one or more functional activities associated with a full-length, wild-type HADH protein, such as antigenic or immunogenic activity, enzymatic activity, ability to bind natural cellular substrates, etc. The functional activity of HADH proteins, derivatives and fragments can be assayed by various methods known to one skilled in the art (Current Protocols in Protein Science (1998) Coligan et al., eds., John Wiley & Sons, Inc., Somerset, N.J.) and as further discussed below. For purposes herein, functionally active fragments also include those fragments that comprise one or more structural domains of an HADH, such as a hydrolase domain or a binding domain. Protein domains can be identified using the PFAM program (Bateman A., et al., Nucleic Acids Res, 1999, 27:260–2; website at pfam.wustl.edu). For example, the hydrolase domain of HADH from GI# 4902680 (SEQ ID NO: 3) is located at approximately amino acid residues 9–212 (PFAM 00702). Methods for obtaining HADH polypeptides are also further described below. In some embodiments, preferred fragments are functionally active, domain-containing fragments comprising at least 25 contiguous amino acids, preferably at least 50, more preferably 75, and most preferably at least 100 contiguous amino acids of any one of SEQ ID NOs:3 or 4 (an HADH). In further preferred embodiments, the fragment comprises the entire hydrolase (functionally active) domain.

The term "HADH nucleic acid" refers to a DNA or RNA molecule that encodes a HADH polypeptide. Preferably, the HADH polypeptide or nucleic acid or fragment thereof is from a human, but can also be an ortholog, or derivative thereof with at least 70% sequence identity, preferably at least 80%, more preferably 85%, still more preferably 90%, and most preferably at least 95% sequence identity with HADH. Normally, orthologs in different species retain the same function, due to presence of one or more protein motifs and/or 3-dimensional structures. Orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849–5856; Huynen M A et al., Genome Research (2000) 10:1204–1210). Programs for multiple sequence alignment, such as CLUSTAL (Thompson J D et al, 1994, Nucleic Acids Res 22:4673–4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. In evolution, when a gene duplication event follows speciation, a single gene in one species, such as *Drosophila*, may correspond to multiple genes (paralogs) in another, such as human. As used herein, the term "orthologs" encompasses paralogs. As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403–410; website at blast.wustl.edu/blast/README.html) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Alternatively, an alignment for nucleic acid sequences is provided by the local homology algorithm of Smith and Waterman (Smith and Waterman, 1981, Advances in Applied Mathematics 2:482–489; database: European Bioinformatics Institute, website at .ebi.ac.uk/MPsrch; Smith and Waterman, 1981, J. of Molec. Biol., 147:195–197; Nicholas et al., 1998, "A Tutorial on Searching Sequence Databases and Sequence Scoring Methods" (website at .psc.edu) and references cited therein.; W. R. Pearson, 1991, Genomics 11:635–650). This algorithm can be applied to amino acid sequences by using the scoring matrix developed by Dayhoff (Dayhoff: Atlas of Protein Sequences and Structure, M. O. Dayhoff ed., 5 suppl. 3:353–358, National Biomedical Research Foundation, Washington, D.C., USA), and normalized by Gribskov (Gribskov 1986 Nucl. Acids Res. 14(6):6745–763). The Smith-Waterman algorithm may be employed where default parameters are used for scoring (for example, gap open penalty of 12, gap extension penalty of two). From the data generated, the "Match" value reflects "sequence identity."

Derivative nucleic acid molecules of the subject nucleic acid molecules include sequences that hybridize to the nucleic acid sequence of SEQ ID NOs:1 or 2. The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of any one of SEQ ID NOs:1 or 2 under stringent hybridization conditions that comprise: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5× Denhardt's solution, 0.05% sodium pyrophosphate and 100 µg/ml herring sperm DNA; hybridization for 18–20 hours at 65° C. in a solution containing 6×SSC, 1× Denhardt's solution, 100 µg/ml yeast tRNA and 0.05% sodium pyrophosphate; and washing of filters at 65° C. for 1 h in a solution containing 0.2×SSC and 0.1% SDS (sodium dodecyl sulfate).

In other embodiments, moderately stringent hybridization conditions are used that comprise: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18–20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS.

Alternatively, low stringency conditions can be used that comprise: incubation for 8 hours to overnight at 37° C. in a solution comprising 20% formamide, 5×SSC, 50 mM sodium phosphate (pH 7.6), 5× Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

Isolation, Production, Expression, and Mis-Expression of HADH Nucleic Acids and Polypeptides HADH nucleic acids and polypeptides, useful for identifying and testing agents that modulate HADH function and for other applications related to the involvement of HADH in the p21 pathway. HADH nucleic acids and derivatives and orthologs thereof may be obtained using any available method. For instance, techniques for isolating cDNA or genomic DNA sequences of interest by screening DNA libraries or by using polymerase chain reaction (PCR) are well known in the art. In general, the particular use for the protein will dictate the particulars of expression, production, and purification methods. For instance, production of proteins for use in screening for modulating agents may require methods that preserve specific biological activities of these proteins, whereas production of proteins for antibody generation may require structural integrity of particular epitopes. Expression of proteins to be purified for screening or antibody production may require the addition of specific tags (e.g., generation of fusion proteins). Overexpression of an HADH protein for assays used to assess HADH function, such as involvement in cell cycle regulation or hypoxic response, may require expression in eukaryotic cell lines capable of these cellular activities. Techniques for the expression, production, and purification of proteins are well known in the art; any suitable means therefore may be used (e.g., Higgins S J and Hames B D (eds.) Protein Expression: A Practical Approach, Oxford University Press Inc., New York 1999; Stanbury P F et al., Principles of Fermentation Technology, $2^{nd}$ edition, Elsevier Science, New York, 1995; Doonan S (ed.) Protein Purification Protocols, Humana Press, New Jersey, 1996; Coligan J E et al, Current Protocols in Protein Science (eds.), 1999, John Wiley & Sons, New York). In particular embodiments, recombinant HADH is expressed in a cell line known to have defective p21 function such as HCT116 colon cancer cells available from American Type Culture Collection (ATCC), Manassas, Va.). The recombinant cells are used in cell-based screening assay systems of the invention, as described further below.

The nucleotide sequence encoding an HADH polypeptide can be inserted into any appropriate expression vector. The necessary transcriptional and translational signals, including promoter/enhancer element, can derive from the native HADH gene and/or its flanking regions or can be heterologous. A variety of host-vector expression systems may be utilized, such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, plasmid, or cosmid DNA. A host cell strain that modulates the expression of, modifies, and/or specifically processes the gene product may be used.

To detect expression of the HADH gene product, the expression vector can comprise a promoter operably linked to an HADH gene nucleic acid, one or more origins of replication, and, one or more selectable markers (e.g. thymidine kinase activity, resistance to antibiotics, etc.). Alternatively, recombinant expression vectors can be identified by assaying for the expression of the HADH gene product based on the physical or functional properties of the HADH protein in in vitro assay systems (e.g. immunoassays).

The HADH protein, fragment, or derivative may be optionally expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. A chimeric product may also be made by protein synthetic techniques, e.g. by use of a peptide synthesizer (Hunkapiller et al., Nature (1984) 310:105–111).

Once a recombinant cell that expresses the HADH gene sequence is identified, the gene product can be isolated and purified using standard methods (e.g. ion exchange, affinity, and gel exclusion chromatography; centrifugation; differential solubility; electrophoresis). Alternatively, native HADH proteins can be purified from natural sources, by standard methods (e.g. immunoaffinity purification). Once a protein is obtained, it may be quantified and its activity measured by appropriate methods, such as immunoassay, bioassay, or other measurements of physical properties, such as crystallography.

The methods of this invention may also use cells that have been engineered for altered expression (mis-expression) of HADH or other genes associated with the p21 pathway. As used herein, mis-expression encompasses ectopic expression, over-expression, under-expression, and non-expression (e.g. by gene knock-out or blocking expression that would otherwise normally occur).

Genetically Modified Animals

Animal models that have been genetically modified to alter HADH expression may be used in in vivo assays to test for activity of a candidate p21 modulating agent, or to further assess the role of HADH in a p21 pathway process such as apoptosis or cell proliferation. Preferably, the altered HADH expression results in a detectable phenotype, such as decreased or increased levels of cell proliferation, angiogenesis, or apoptosis compared to control animals having normal HADH expression. The genetically modified animal may additionally have altered p21 expression (e.g. p21 knockout). Preferred genetically modified animals are mammals such as primates, rodents (preferably mice), cows, horses, goats, sheep, pigs, dogs and cats. Preferred non-mammalian species include zebrafish, *C. elegans*, and *Drosophila*. Preferred genetically modified animals are transgenic animals having a heterologous nucleic acid sequence present as an extrachromosomal element in a portion of its cells, i.e. mosaic animals (see, for example, techniques described by Jakobovits, 1994, Curr. Biol. 4:761–763.) or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well known in the art (for transgenic mice see Brinster et al., Proc. Nat. Acad. Sci. USA 82: 4438–4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. , 4,945,050, by Sandford et al.; for transgenic *Drosophila* see Rubin and Spradling, Science (1982) 218:348–53 and U.S. Pat. No. 4,670,388; for transgenic insects see Berghammer A. J. et al., A Universal Marker for Transgenic Insects (1999) Nature 402:370–371; for transgenic Zebrafish see Lin S., Transgenic Zebrafish, Methods Mol Biol. (2000);136:375–3830); for microinjection procedures for fish, amphibian eggs and birds see Houdebine and Chourrout, Experientia (1991) 47:897–905; for transgenic rats see Hammer et al., Cell (1990) 63:1099–1112; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1997) Nature 385:810–813; and PCT International Publication Nos. WO 97/07668 and WO 97/07669).

In one embodiment, the transgenic animal is a "knock-out" animal having a heterozygous or homozygous alteration in the sequence of an endogenous HADH gene that results in a decrease of HADH function, preferably such that HADH expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse HADH gene is used to construct a homologous recombination vector suitable for altering an endogenous HADH gene in the mouse genome. Detailed methodologies for homologous recombination in mice are available (see Capecchi, Science (1989) 244:1288–1292; Joyner et al., Nature (1989) 338:153–156). Procedures for the production of non-rodent transgenic mammals and other animals are also available (Houdebine and Chourrout, supra; Pursel et al., Science (1989) 244:1281–1288; Simms et al., Bio/Technology (1988) 6:179–183). In a preferred embodiment, knock-out animals, such as mice harboring a knockout of a specific gene, may be used to produce antibodies against the human counterpart of the gene that has been knocked out (Claesson M H et al., (1994) Scan J Immunol 40:257–264; Declerck P J et al., (1995) J Biol Chem. 270:8397–400).

In another embodiment, the transgenic animal is a "knock-in" animal having an alteration in its genome that results in altered expression (e.g., increased (including ectopic) or decreased expression) of the HADH gene, e.g., by introduction of additional copies of HADH, or by operatively inserting a regulatory sequence that provides for altered expression of an endogenous copy of the HADH gene. Such regulatory sequences include inducible, tissue-specific, and constitutive promoters and enhancer elements. The knock-in can be homozygous or heterozygous.

Transgenic nonhuman animals can also be produced that contain selected systems allowing for regulated expression of the transgene. One example of such a system that may be produced is the cre/loxP recombinase system of bacteriophage P1 (Lakso et al., PNAS (1992) 89:6232–6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of *Saccharomyces cerevisiae* (O'Gorman et al. (1991) Science 251:1351–1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83–6).

The genetically modified animals can be used in genetic studies to further elucidate the p21 pathway, as animal models of disease and disorders implicating defective p21 function, and for in vivo testing of candidate therapeutic agents, such as those identified in screens described below. The candidate therapeutic agents are administered to a genetically modified animal having altered HADH function and phenotypic changes are compared with appropriate control animals such as genetically modified animals that receive placebo treatment, and/or animals with unaltered HADH expression that receive candidate therapeutic agent.

In addition to the above-described genetically modified animals having altered HADH function, animal models having defective p21 function (and otherwise normal HADH function), can be used in the methods of the present invention. For example, a p21 knockout mouse can be used to assess, in vivo, the activity of a candidate p21 modulating agent identified in one of the in vitro assays described below. p21 knockout mouse are described in the literature (Umanoff H, et al., Proc Natl Acad Sci U S A 1995 Feb 28;92(5): 1709–13). Preferably, the candidate p21 modulating agent when administered to a model system with cells defective in p21 function, produces a detectable phenotypic change in the model system indicating that the p21 function is restored, i.e., the cells exhibit normal cell cycle progression.

Modulating Agents

The invention provides methods to identify agents that interact with and/or modulate the function of HADH and/or the p21 pathway. Modulating agents identified by the methods are also part of the invention. Such agents are useful in a variety of diagnostic and therapeutic applications associated with the p21 pathway, as well as in further analysis of the HADH protein and its contribution to the p21 pathway. Accordingly, the invention also provides methods for modulating the p21 pathway comprising the step of specifically modulating HADH activity by administering a HADH-interacting or -modulating agent.

As used herein, an "HADH-modulating agent" is any agent that modulated HADH function, for example, an agent that interacts with HADH to inhibit or enhance HADH activity or otherwise affect normal HADH function. HADH function can be affected at any level, including transcription, protein expression, protein localization, and cellular or extra-cellular activity. In a preferred embodiment, the HADH-modulating agent specifically modulates the function of the HADH. The phrases "specific modulating agent", "specifically modulates", etc., are used herein to refer to modulating agents that directly bind to the HADH polypeptide or nucleic acid, and preferably inhibit, enhance, or otherwise alter, the function of the HADH. These phrases also encompass modulating agents that alter the interaction of the HADH with a binding partner, substrate, or cofactor (e.g. by binding to a binding partner of an HADH, or to a protein/binding partner complex, and altering HADH function). In a further preferred embodiment, the HADH-modulating agent is a modulator of the p21 pathway (e.g. it restores and/or upregulates p21 function) and thus is also a p21-modulating agent.

Preferred HADH-modulating agents include small molecule compounds; HADH-interacting proteins, including antibodies and other biotherapeutics; and nucleic acid modulators such as antisense and RNA inhibitors. The modulating agents may be formulated in pharmaceutical compositions, for example, as compositions that may comprise other active ingredients, as in combination therapy, and/or suitable carriers or excipients. Techniques for formulation and administration of the compounds may be found in "Remington's Pharmaceutical Sciences" Mack Publishing Co., Easton, Pa., 19$^{th}$ edition.

Small Molecule Modulators

Small molecules are often preferred to modulate function of proteins with enzymatic function, and/or containing protein interaction domains. Chemical agents, referred to in the art as "small molecule" compounds are typically organic, non-peptide molecules, having a molecular weight less than 10,000, preferably less than 5,000, more preferably less than 1,000, and most preferably less than 500. This class of modulators includes chemically synthesized molecules, for instance, compounds from combinatorial chemical libraries. Synthetic compounds may be rationally designed or identified based on known or inferred properties of the HADH protein or may be identified by screening compound libraries. Alternative appropriate modulators of this class are natural products, particularly secondary metabolites from organisms such as plants or fungi, which can also be identified by screening compound libraries for HADH-modulating activity. Methods for generating and obtaining compounds are well known in the art (Schreiber S L, Science (2000) 151: 1964–1969; Radmann J and Gunther J, Science (2000) 151:1947–1948).

Small molecule modulators identified from screening assays, as described below, can be used as lead compounds from which candidate clinical compounds may be designed, optimized, and synthesized. Such clinical compounds may have utility in treating pathologies associated with the p21 pathway. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

Specific HADH-interacting proteins are useful in a variety of diagnostic and therapeutic applications related to the p21 pathway and related disorders, as well as in validation assays for other HADH-modulating agents. In a preferred embodiment, HADH-interacting proteins affect normal HADH function, including transcription, protein expression, protein localization, and cellular or extra-cellular activity. In another embodiment, HADH-interacting proteins are useful in detecting and providing information about the function of HADH proteins, as is relevant to p21 related disorders, such as cancer (e.g., for diagnostic means).

An HADH-interacting protein may be endogenous, i.e. one that naturally interacts genetically or biochemically with an HADH, such as a member of the HADH pathway that modulates HADH expression, localization, and/or activity. HADH-modulators include dominant negative forms of HADH-interacting proteins and of HADH proteins themselves. Yeast two-hybrid and variant screens offer preferred methods for identifying endogenous HADH-interacting proteins (Finley, R. L. et al. (1996) in DNA Cloning-Expression Systems: A Practical Approach, eds. Glover D. & Hames B. D (Oxford University Press, Oxford, England), pp. 169–203; Fashema S F et al., Gene (2000) 250:1–14; Drees B L Curr Opin Chem Biol (1999) 3:64–70; Vidal M and Legrain P Nucleic Acids Res (1999) 27:919–29; and U.S. Pat. No. 5,928,868). Mass spectrometry is an alternative preferred method for the elucidation of protein complexes (reviewed in, e.g., Pandley A and Mann M, Nature (2000) 405:837–846; Yates J R 3$^{rd}$, Trends Genet (2000) 16:5–8).

An HADH-interacting protein may be an exogenous protein, such as an HADH-specific antibody or a T-cell antigen receptor (see, e.g., Harlow and Lane (1988) Antibodies, A Laboratory Manual, Cold Spring Harbor Laboratory; Harlow and Lane (1999) Using antibodies: a laboratory manual. Cold Spring Harbor, N.Y.: Cold Spring Harbor Laboratory Press). HADH antibodies are further discussed below.

In preferred embodiments, an HADH-interacting protein specifically binds an HADH protein. In alternative preferred embodiments, an HADH-modulating agent binds an HADH substrate, binding partner, or cofactor.

Antibodies

In another embodiment, the protein modulator is an HADH specific antibody agonist or antagonist. The antibodies have therapeutic and diagnostic utilities, and can be used in screening assays to identify HADH modulators. The antibodies can also be used in dissecting the portions of the HADH pathway responsible for various cellular responses and in the general processing and maturation of the HADH.

Antibodies that specifically bind HADH polypeptides can be generated using known methods. Preferably the antibody is specific to a mammalian ortholog of HADH polypeptide, and more preferably, to human HADH. Antibodies may be polyclonal, monoclonal (mAbs), humanized or chimeric antibodies, single chain antibodies, Fab fragments, F(ab').sub.2 fragments, fragments produced by a FAb expression library, anti-idiotypic (anti-Id) antibodies, and epitope-binding fragments of any of the above. Epitopes of HADH which are particularly antigenic can be selected, for example, by routine screening of HADH polypeptides for antigenicity or by applying a theoretical method for selecting antigenic regions of a protein (Hopp and Wood (1981), Proc. Nati. Acad. Sci. U.S.A. 78:3824–28; Hopp and Wood, (1983) Mol. Immunol. 20:483–89; Sutcliffe et al., (1983) Science 219:660–66) to the amino acid sequence shown in SEQ ID NOs:3 or 4. Monoclonal antibodies with affinities of $10^8$ $M^{-1}$ preferably $10^9$ $M^{-1}$ to $10^{10}$ $M^{-1}$, or stronger can be made by standard procedures as described (Harlow and Lane, supra; Goding (1986) Monoclonal Antibodies: Principles and Practice (2d ed) Academic Press, New York; and U.S. Pat. Nos. 4,381,292; 4,451,570; and 4,618,577). Antibodies may be generated against crude cell extracts of HADH or substantially purified fragments thereof. If HADH fragments are used, they preferably comprise at least 10, and more preferably, at least 20 contiguous amino acids of an HADH protein. In a particular embodiment, HADH-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of HADH-specific antibodies is assayed by an appropriate assay such as a solid phase enzyme-linked immunosorbant assay (ELISA) using immobilized corresponding HADH polypeptides. Other assays, such as radioimmunoassays or fluorescent assays might also be used.

Chimeric antibodies specific to HADH polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851–6855; Neuberger et al., Nature (1984) 312:604–608; Takeda et al., Nature (1985) 31:452–454). Humanized antibodies, which are a form of chimeric antibodies, can be generated by grafting complementarydetermining regions (CDRs) (Carlos, T. M., J. M. Harlan. 1994. Blood 84:2068–2101) of mouse antibodies into a background of human framework regions and constant regions by recombinant DNA technology (Riechmann L M, et al., 1988 Nature 323: 323–327). Humanized antibodies contain ~10% murine sequences and ~90% human sequences, and thus further reduce or eliminate immunogenicity, while retaining the antibody specificities (Co M S, and Queen C. 1991 Nature 351: 501–501; Morrison S L. 1992 Ann. Rev. Immun. 10:239–265). Humanized antibodies and methods of their production are well-known in the art (U.S. Pat. Nos. 5,530,101, 5,585,089, 5,693,762, and 6,180,370).

HADH-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423–426; Huston et al., Proc. Natl. Acad. Sci. USA (1988) 85:5879–5883; and Ward et al., Nature (1989) 334:544–546).

Other suitable techniques for antibody production involve in vitro exposure of lymphocytes to the antigenic polypeptides or alternatively to selection of libraries of antibodies in phage or similar vectors (Huse et al., Science (1989) 246:1275–1281). As used herein, T-cell antigen receptors are included within the scope of antibody modulators (Harlow and Lane, 1988, supra).

The polypeptides and antibodies of the present invention may be used with or without modification. Frequently, antibodies will be labeled by joining, either covalently or non-covalently, a substance that provides for a detectable signal, or that is toxic to cells that express the targeted protein (Menard S, et al., Int J. Biol Markers (1989) 4:131–134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816,567). Antibodies to cytoplasmic polypeptides may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg–to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml to about 10 mg/ml. Immunotherapeutic methods are further described in the literature (U.S. Pat. No. 5,859,206; WO0073469).

Nucleic Acid Modulators

Other preferred HADH-modulating agents comprise nucleic acid molecules, such as antisense oligomers or double stranded RNA (dsRNA), which generally inhibit HADH activity. Preferred nucleic acid modulators interfere with the function of the HADH nucleic acid such as DNA replication, transcription, translocation of the HADH RNA to the site of protein translation, translation of protein from the HADH RNA, splicing of the HADH RNA to yield one or more mRNA species, or catalytic activity which may be engaged in or facilitated by the HADH RNA.

In one embodiment, the antisense oligomer is an oligonucleotide that is sufficiently complementary to an HADH mRNA to bind to and prevent translation, preferably by binding to the 5' untranslated region. HADH-specific antisense oligonucleotides, preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA or a chimeric mixture or derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphothioate morpholino oligomer (PMO). PMOs are assembled from four different morpholino subunits, each of which contain one of four genetic bases (A, C, G, or T) linked to a six-membered morpholine ring. Polymers of these subunits are joined by non-ionic phosphodiamidate intersubunit linkages. Details of how to make and use PMOs and other antisense oligomers are well known in the art (e.g. see WO99/18193; Probst J C, Antisense Oligodeoxynucleotide and Ribozyme Design, Methods. (2000) 22(3): 271–281; Summerton J, and Weller D. 1997 Antisense Nucleic Acid Drug Dev.: 7:187–95; U.S. Pat. No. 5,235,033; and U.S. Pat No. 5,378,841).

Alternative preferred HADH nucleic acid modulators are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in C. elegans, Drosophila, plants, and humans are known in the art (Fire A, et al., 1998 Nature 391:806–811; Fire, A. Trends Genet. 15, 358–363 (1999); Sharp, P. A. RNA interference 2001. Genes Dev. 15, 485–490 (2001); Hammond, S. M., et al., Nature Rev. Genet. 2, 110–1119 (2001); Tuschl, T. Chem. Biochem. 2, 239–245 (2001); Hamilton, A. et al., Science 286, 950–952 (1999); Hammond, S. M., et al., Nature 404, 293–296 (2000); Zamore, P. D., et al., Cell 101, 25–33 (2000); Bernstein, E., et al., Nature 409, 363–366 (2001); Elbashir, S. M., et al., Genes Dev. 15, 188–200 (2001); WO0129058; WO9932619; Elbashir S M, et al., 2001 Nature 411:494–498).

Nucleic acid modulators are commonly used as research reagents, diagnostics, and therapeutics. For example, antisense oligonucleotides, which are able to inhibit gene expression with exquisite specificity, are often used to elucidate the function of particular genes (see, for example, U.S. Pat. No. 6,165,790). Nucleic acid modulators are also used, for example, to distinguish between functions of various members of a biological pathway. For example, antisense oligomers have been employed as therapeutic moieties in the treatment of disease states in animals and man and have been demonstrated in numerous clinical trials to be safe and effective (Milligan J F, et al, Current Concepts in Antisense Drug Design, J Med Chem. (1993) 36:1923–1937; Tonkinson J L et al., Antisense Oligodeoxynucleotides as Clinical Therapeutic Agents, Cancer Invest. (1996) 14:54–65). Accordingly, in one aspect of the invention, an HADH-specific nucleic acid modulator is used in an assay to further elucidate the role of the HADH in the p21 pathway, and/or its relationship to other members of the pathway. In another aspect of the invention, an HADH-specific antisense oligomer is used as a therapeutic agent for treatment of p21-related disease states.

Assay Systems

The invention provides assay systems and screening methods for identifying specific modulators of HADH activity. As used herein, an "assay system" encompasses all the components required for performing and analyzing results of an assay that detects and/or measures a particular event. In general, primary assays are used to identify or confirm a modulator's specific biochemical or molecular effect with respect to the HADH nucleic acid or protein. In general, secondary assays further assess the activity of a HADH modulating agent identified by a primary assay and may confirm that the modulating agent affects HADH in a manner relevant to the p21 pathway. In some cases, HADH modulators will be directly tested in a secondary assay.

In a preferred embodiment, the screening method comprises contacting a suitable assay system comprising an HADH polypeptide or nucleic acid with a candidate agent under conditions whereby, but for the presence of the agent, the system provides a reference activity (e.g. binding activity), which is based on the particular molecular event the screening method detects. A statistically significant difference between the agent-biased activity and the reference activity indicates that the candidate agent modulates HADH activity, and hence the p21 pathway. The HADH polypeptide or nucleic acid used in the assay may comprise any of the nucleic acids or polypeptides described above.

Primary Assays

The type of modulator tested generally determines the type of primary assay.

Primary Assays for Small Molecule Modulators

For small molecule modulators, screening assays are used to identify candidate modulators. Screening assays may be cell-based or may use a cell-free system that recreates or retains the relevant biochemical reaction of the target protein (reviewed in Sittampalam G S et al., Curr Opin Chem Biol (1997) 1:384–91 and accompanying references). As used herein the term "cell-based" refers to assays using live cells, dead cells, or a particular cellular fraction, such as a membrane, endoplasmic reticulum, or mitochondrial fraction. The term "cell free" encompasses assays using substantially purified protein (either endogenous or recombinantly produced), partially purified or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicty and changes in cellular morphology or other cellular characteristics. Appropriate screening assays may use a wide range of detection methods including fluorescent, radioactive, colorimetric, spectrophotometric, and amperometric methods, to provide a read-out for the particular molecular event detected.

Cell-based screening assays usually require systems for recombinant expression of HADH and any auxiliary proteins demanded by the particular assay. Appropriate methods for generating recombinant proteins produce sufficient quantities of proteins that retain their relevant biological activities and are of sufficient purity to optimize activity and assure assay reproducibility. Yeast two-hybrid and variant screens, and mass spectrometry provide preferred methods for determining protein-protein interactions and elucidation of protein complexes. In certain applications, when HADH-interacting proteins are used in screens to identify small molecule modulators, the binding specificity of the interacting protein to the HADH protein may be assayed by various known methods such as substrate processing (e.g. ability of the candidate HADH-specific binding agents to function as negative effectors in HADH-expressing cells), binding equilibrium constants (usually at least about $10^7$ $M^{-1}$, preferably at least about $10^8$ $M^{-1}$, more preferably at least about $10^9$ $M^{-1}$), and immunogenicity (e.g. ability to elicit HADH specific antibody in a heterologous host such as a mouse, rat, goat or rabbit). For enzymes and receptors, binding may be assayed by, respectively, substrate and ligand processing.

The screening assay may measure a candidate agent's ability to specifically bind to or modulate activity of a HADH polypeptide, a fusion protein thereof, or to cells or membranes bearing the polypeptide or fusion protein. The HADH polypeptide can be full length or a fragment thereof that retains functional HADH activity. The HADH polypeptide may be fused to another polypeptide, such as a peptide tag for detection or anchoring, or to another tag. The HADH polypeptide is preferably human HADH, or is an ortholog or derivative thereof as described above. In a preferred embodiment, the screening assay detects candidate agent-based modulation of HADH interaction with a binding target, such as an endogenous or exogenous protein or other substrate that has HADH-specific binding activity, and can be used to assess normal HADH gene function.

Suitable assay formats that may be adapted to screen for HADH modulators are known in the art. Preferred screening assays are high throughput or ultra high throughput and thus provide automated, cost-effective means of screening compound libraries for lead compounds (Fernandes P B, Curr Opin Chem Biol (1998) 2:597–603; Sundberg S A, Curr Opin Biotechnol 2000, 11:47–53). In one preferred embodiment, screening assays uses fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730–4; Fernandes P B, supra; Hertzberg R P and Pope A J, Curr Opin Chem Biol (2000) 4:445–451).

A variety of suitable assay systems may be used to identify candidate HADH and p21 pathway modulators (e.g. U.S. Pat. Nos. 5,550,019 and 6,133,437 (apoptosis assays), among others). Specific preferred assays are described in more detail below.

Hydrolase assays. Hydrolases catalyze the hydrolysis of a substrate such as esterases, lipases, peptidases, nucleotidases, and phosphatases, among others. Enzyme activity assays may be used to measure hydrolase activity. The activity of the enzyme is determined in presence of excess substrate, by spectrophotometrically measuring the rate of appearance of reaction products. High throughput arrays and assays for hydrolases are known to those skilled in the art (Park C B and Clark D S (2002) Biotech Bioeng 78:229–235).

Apoptosis Assays

Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:4730–41). An apoptosis assay system may comprise a cell that expresses an HADH, and that optionally has defective p21 function (e.g. p21 is over-expressed or under-expressed relative to wild-type cells). A test agent can be added to the apoptosis assay system and changes in induction of apoptosis relative to controls where no test agent is added, identify candidate p21 modulating agents. In some embodiments of the invention, an apoptosis assay may be used as a secondary assay to test a candidate p21 modulating agents that is initially identified using a cell-free assay system. An apoptosis assay may also be used to test whether HADH function plays a direct role in apoptosis. For example, an apoptosis assay may be performed on cells that over- or under-express HADH relative to wild type cells. Differences in apoptotic response compared to wild type cells suggests that the HADH plays a direct role in the apoptotic response. Apoptosis assays are described further in U.S. Pat. No. 6,133,437.

Cell Proliferation and Cell Cycle Assays

Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79), or by other means.

Cell Proliferation may also be examined using [$^3$H]-thymidine incorporation (Chen, J., 1996, Oncogene 13:1395–403; Jeoung, J., 1995, J. Biol. Chem. 270:18367–73). This assay allows for quantitative characterization of S-phase DNA syntheses. In this assay, cells synthesizing DNA will incorporate [$^3$H]-thymidine into newly synthesized DNA. Incorporation can then be measured by standard techniques such as by counting of radio-isotope in a scintillation counter (e.g., Beckman LS 3800 Liquid Scintillation Counter).

Cell proliferation may also be assayed by colony formation in soft agar (Sambrook et al., Molecular Cloning, Cold Spring Harbor (1989)). For example, cells transformed with HADH are seeded in soft agar plates, and colonies are measured and counted after two weeks incubation.

Involvement of a gene in the cell cycle may be assayed by flow cytometry (Gray J W et al. (1986) Int J Radiat Biol Relat Stud Phys Chem Med 49:237–55). Cells transfected with an HADH may be stained with propidium iodide and evaluated in a flow cytometer (available from Becton Dickinson).

Accordingly, a cell proliferation or cell cycle assay system may comprise a cell that expresses an HADH, and that optionally has defective p21 function (e.g. p21 is over-expressed or under-expressed relative to wild-type cells). A test agent can be added to the assay system and changes in cell proliferation or cell cycle relative to controls where no test agent is added, identify candidate p21 modulating agents. In some embodiments of the invention, the cell proliferation or cell cycle assay may be used as a secondary assay to test a candidate p21 modulating agents that is initially identified using another assay system such as a cell-free assay system. A cell proliferation assay may also be used to test whether HADH function plays a direct role in cell proliferation or cell cycle. For example, a cell proliferation or cell cycle assay may be performed on cells that over- or under-express HADH relative to wild type cells. Differences in proliferation or cell cycle compared to wild type cells suggests that the HADH plays a direct role in cell proliferation or cell cycle.

Angiogenesis

Angiogenesis may be assayed using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HTS FluoroBlock cell culture inserts to measure migration of cells through membranes in presence or absence of angiogenesis enhancer or suppressors; and tubule formation assays based on the formation of tubular structures by endothelial cells on Matrigel® (Becton Dickinson). Accordingly, an angiogenesis assay system may comprise a cell that expresses an HADH, and that optionally has defective p21 function (e.g. p21 is over-expressed or under-expressed relative to wild-type cells). A test agent can be added to the angiogenesis assay system and changes in angiogenesis relative to controls where no test agent is added, identify candidate p21 modulating agents. In some embodiments of the invention, the angiogenesis assay may be used as a secondary assay to test a candidate p21 modulating agents that is initially identified using another assay system. An angiogenesis assay may also be used to test whether HADH function plays a direct role in cell proliferation. For example, an angiogenesis assay may be performed on cells that over- or under-express HADH relative to wild type cells. Differences in angiogenesis compared to wild type cells suggests that the HADH plays a direct role in angiogenesis.

Hypoxic Induction

The alpha subunit of the transcription factor, hypoxia inducible factor-1 (HIF-1), is upregulated in tumor cells following exposure to hypoxia in vitro. Under hypoxic conditions, HIF-1 stimulates the expression of genes known to be important in tumour cell survival, such as those encoding glyolytic enzymes and VEGF. Induction of such genes by hypoxic conditions may be assayed by growing cells transfected with HADH in hypoxic conditions (such as with 0.1% $O_2$, 5% $CO_2$, and balance $N_2$, generated in a Napco 7001 incubator (Precision Scientific)) and normoxic conditions, followed by assessment of gene activity or expression by Taqman®. For example, a hypoxic induction assay system may comprise a cell that expresses an HADH, and that optionally has a mutated p21 (e.g. p21 is over-expressed or under-expressed relative to wild-type cells). A test agent can be added to the hypoxic induction assay system and changes in hypoxic response relative to controls where no test agent is added, identify candidate p21 modulating agents. In some embodiments of the invention, the hypoxic induction assay may be used as a secondary assay to test a candidate p21 modulating agents that is initially identified using another assay system. A hypoxic induction assay may also be used to test whether HADH function plays a direct role in the hypoxic response. For example, a hypoxic induction assay may be performed on cells that over- or under-express HADH relative to wild type cells. Differences in hypoxic response compared to wild type cells suggests that the HADH plays a direct role in hypoxic induction.

Cell Adhesion

Cell adhesion assays measure adhesion of cells to purified adhesion proteins, or adhesion of cells to each other, in presence or absence of candidate modulating agents. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays measure the ability of agents to modulate binding of cell adhesion proteins with their native ligands. These assays use cells that naturally or recombinantly express the adhesion protein of choice. In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only the binding specificity of the peptides and modulators against cell lines are determined, but also the functional cell signaling of attached cells using immunofluorescence techniques in situ on the microchip is measured (Falsey J R et al., Bioconjug Chem. 2001 May–June; 12(3):346–53).

Primary Assays for Antibody Modulators

For antibody modulators, appropriate primary assays test is a binding assay that tests the antibody's affinity to and specificity for the HADH protein. Methods for testing antibody affinity and specificity are well known in the art (Harlow and Lane, 1988, 1999, supra). The enzyme-linked immunosorbant assay (ELISA) is a preferred method for detecting HADH-specific antibodies; others include FACS assays, radioimmunoassays, and fluorescent assays.

Primary Assays for Nucleic Acid Modulators

For nucleic acid modulators, primary assays may test the ability of the nucleic acid modulator to inhibit or enhance HADH gene expression, preferably mRNA expression. In general, expression analysis comprises comparing HADH expression in like populations of cells (e.g., two pools of cells that endogenously or recombinantly express HADH) in the presence and absence of the nucleic acid modulator. Methods for analyzing mRNA and protein expression are well known in the art. For instance, Northern blotting, slot blotting, ribonuclease protection, quantitative RT-PCR (e.g., using the TaqMan®, PE Applied Biosystems), or microarray analysis may be used to confirm that HADH mRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112–125; Kallioniemi O P, Ann Med 2001, 33:142–147; Blohm D H and Guiseppi-Elie, A Curr Opin Biotechnol 2001, 12:41–47). Protein expression may also be monitored. Proteins are most commonly detected with specific antibodies or antisera directed against either the HADH protein or specific peptides. A variety of means including Western blotting, ELISA, or in situ detection, are available (Harlow E and Lane D, 1988 and 1999, supra).

Secondary Assays

Secondary assays may be used to further assess the activity of HADH-modulating agent identified by any of the above methods to confirm that the modulating agent affects HADH in a manner relevant to the p21 pathway. As used herein, HADH-modulating agents encompass candidate clinical compounds or other agents derived from previously identified modulating agent. Secondary assays can also be used to test the activity of a modulating agent on a particular genetic or biochemical pathway or to test the specificity of the modulating agent's interaction with HADH.

Secondary assays generally compare like populations of cells or animals (e.g., two pools of cells or animals that endogenously or recombinantly express HADH) in the presence and absence of the candidate modulator. In general, such assays test whether treatment of cells or animals with a candidate HADH-modulating agent results in changes in the p21 pathway in comparison to untreated (or mock- or placebo-treated) cells or animals. Certain assays use "sensitized genetic backgrounds", which, as used herein, describe cells or animals engineered for altered expression of genes in the p21 or interacting pathways.

Cell-Based Assays

Cell based assays may use a variety of a cell line known to have defective p21 function such as HCT116 colon cancer cells available from American Type Culture Collection (ATCC), Manassas, Va.). Cell based assays may detect endogenous p21 pathway activity or may rely on recombinant expression of p21 pathway components. Any of the aforementioned assays may be used in this cell-based format. Candidate modulators are typically added to the cell media but may also be injected into cells or delivered by any other efficacious means.

Animal Assays

A variety of non-human animal models of normal or defective p21 pathway may be used to test candidate HADH modulators. Models for defective p21 pathway typically use genetically modified animals that have been engineered to mis-express (e.g., over-express or lack expression in) genes involved in the p21 pathway. Assays generally require systemic delivery of the candidate modulators, such as by oral administration, injection, etc.

In a preferred embodiment, p21 pathway activity is assessed by monitoring neovascularization and angiogenesis. Animal models with defective and normal p21 are used to test the candidate modulator's affect on HADH in Matrigel® assays. Matrigel® is an extract of basement membrane proteins, and is composed primarily of laminin, collagen IV, and heparin sulfate proteoglycan. It is provided as a sterile liquid at 4° C., but rapidly forms a solid gel at 37° C. Liquid Matrigel® is mixed with various angiogenic agents, such as bFGF and VEGF, or with human tumor cells which overexpress the HADH. The mixture is then injected subcutaneously(SC) into female athymic nude mice (Taconic, Germantown, N.Y.) to support an intense vascular response. Mice with Matrigel® pellets may be dosed via oral (PO), intraperitoneal (IP), or intravenous (IV) routes with the candidate modulator. Mice are euthanized 5–12 days post-injection, and the Matrigel® pellet is harvested for hemoglobin analysis (Sigma plasma hemoglobin kit). Hemoglobin content of the gel is found to correlate the degree of neovascularization in the gel.

In another preferred embodiment, the effect of the candidate modulator on HADH is assessed via tumorigenicity assays. In one example, xenograft human tumors are implanted SC into female athymic mice, 6–7 week old, as single cell suspensions either from a pre-existing tumor or from in vitro culture. The tumors which express the HADH endogenously are injected in the flank, $1 \times 10^5$ to $1 \times 10^7$ cells per mouse in a volume of 100 µL using a 27 gauge needle. Mice are then ear tagged and tumors are measured twice weekly. Candidate modulator treatment is initiated on the day the mean tumor weight reaches 100 mg. Candidate modulator is delivered IV, SC, IP, or PO by bolus administration. Depending upon the pharmacokinetics of each unique candidate modulator, dosing can be performed multiple times per day. The tumor weight is assessed by measuring perpendicular diameters with a caliper and calculated by multiplying the measurements of diameters in two dimensions. At the end of the experiment, the excised tumors maybe utilized for biomarker identification or further analyses. For immunohistochemistry staining, xenograft tumors are fixed in 4% paraformaldehyde, 0.1M phosphate, pH 7.2, for 6 hours at 4° C., immersed in 30% sucrose in PBS, and rapidly frozen in isopentane cooled with liquid nitrogen.

Diagnostic and Therapeutic Uses

Specific HADH-modulating agents are useful in a variety of diagnostic and therapeutic applications where disease or disease prognosis is related to defects in the p21 pathway, such as angiogenic, apoptotic, or cell proliferation disorders. Accordingly, the invention also provides methods for modulating the p21 pathway in a cell, preferably a cell predetermined to have defective or impaired p21 function (e.g. due to overexpression, underexpression, or misexpression of p21, or due to gene mutations), comprising the step of administering an agent to the cell that specifically modulates HADH activity. Preferably, the modulating agent produces a detectable phenotypic change in the cell indicating that the p21 function is restored. The phrase "function is restored", and equivalents, as used herein, means that the desired phenotype is achieved, or is brought closer to normal compared to untreated cells. For example, with restored p21 function, cell proliferation and/or progression through cell cycle may normalize, or be brought closer to normal relative to untreated cells. The invention also provides methods for treating disorders or disease associated with impaired p21 function by administering a therapeutically effective amount of an HADH-modulating agent that modulates the p21 pathway. The invention further provides methods for modulating HADH function in a cell, preferably a cell predetermined to have defective or impaired HADH function, by administering an HADH-modulating agent. Additionally, the invention provides a method for treating disorders or disease associated with impaired HADH function by administering a therapeutically effective amount of an HADH-modulating agent.

The discovery that HADH is implicated in p21 pathway provides for a variety of methods that can be employed for the diagnostic and prognostic evaluation of diseases and disorders involving defects in the p21 pathway and for the identification of subjects having a predisposition to such diseases and disorders.

Various expression analysis methods can be used to diagnose whether HADH expression occurs in a particular sample, including Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112–125; Kallioniemi O P, Ann Med 2001, 33:142–147; Blohm and Guiseppi-Elie, Curr Opin Biotechnol 2001, 12:41–47). Tissues having a disease or disorder implicating defective p21 signaling that express an HADH, are identified as amenable to treatment with an HADH modulating agent. In a preferred application, the p21 defective tissue overexpresses an HADH relative to normal tissue. For example, a Northern blot analysis of mRNA from tumor and normal cell lines, or from tumor and matching normal tissue samples from the same patient, using full or partial HADH cDNA sequences as probes, can determine whether particular tumors express or overexpress HADH. Alternatively, the TaqMan® is used for quantitative RT-PCR analysis of HADH expression in cell lines, normal tissues and tumor samples (PE Applied Biosystems).

Various other diagnostic methods may be performed, for example, utilizing reagents such as the HADH oligonucleotides, and antibodies directed against an HADH, as described above for: (1) the detection of the presence of HADH gene mutations, or the detection of either over- or under-expression of HADH mRNA relative to the non-disorder state; (2) the detection of either an over- or an under-abundance of HADH gene product relative to the non-disorder state; and (3) the detection of perturbations or abnormalities in the signal transduction pathway mediated by HADH.

Thus, in a specific embodiment, the invention is drawn to a method for diagnosing a disease or disorder in a patient that is associated with alterations in HADH expression, the method comprising: a) obtaining a biological sample from the patient; b) contacting the sample with a probe for HADH expression; c) comparing results from step (b) with a control; and d) determining whether step (c) indicates a likelihood of the disease or disorder. Preferably, the disease is cancer, most preferably colon or ovarian cancer. The probe may be either DNA or protein, including an antibody.

EXAMPLES

The following experimental section and examples are offered by way of illustration and not by way of limitation.

I. *Drosophila* p21 Screen

An overexpression screen was carried out in *Drosophila* to identify genes that interact with the cyclin dependent kinase inhibitor, p21 (Bourne H R, et al., Nature (1990) 348(6297):125–132; Marshall C J, Trends Genet (1991) 7(3):91–95). Expression of the p21 gene in the eye causes deterioration of normal eye morphology. Modifiers of the eye phenotype were identified as members of the p21 pathway. CG 15771 was a suppressor of the small eye defect.

BLAST analysis (Altschul et al., supra) was employed to identify Targets from *Drosophila* modifiers. For example, a representative sequence from HADH (GI# 4902680, SEQ ID NO:3) shares 34% amino acid identity with the *Drosophila* CG 15771.

Various domains, signals, and functional subunits in proteins were analyzed using the PSORT (Nakai K., and Horton P., Trends Biochem Sci, 1999, 24:34–6; Kenta Nakai, Protein sorting signals and prediction of subcellular localization, Adv. Protein Chem. 54, 277–344 (2000)), PFAM (Bateman A., et al., Nucleic Acids Res, 1999, 27:260–2), SMART (Ponting C P, et al., SMART: identification and annotation of domains from signaling and extracellular protein sequences. Nucleic Acids Res. 1999 Jan 1;27(1):229–32), TM-HMM (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175–182 Ed J. Glasgow, T. Littlejohn, F. Major, R. Lathrop, D. Sankoff, and C. Sensen Menlo Park, Calif.: AAAI Press, 1998), and clust (Remm M, and Sonnhammer E. Classification of transmembrane protein families in the *Caenorhabditis elegans* genome and identification of human orthologs. Genome Res. 2000 November; 10(11): 1679–89) programs. For example, the hydrolase domain of HADH from GI# 4902680 (SEQ ID NO:4) is located at approximately amino acid residues 9–212 (PFAM 00702).

Detailed functional analysis of SEQ ID NO:4 indicated that HADH appears to be a member of the family of the HADH aspartyl-phosphate utilizing phosphohydrolases/phosphotransferases. We used Threading algorithm (Proceryon, N.Y.) to identify structure family relationship of HADH. Threading alignment identified several key residues for members of this family: D12, T16, T131, N132, K164, D189, T193, D194. In SEQ ID NO:4, D12 is highly conserved, and is the site of phosphorylation; T16 is somewhat variable, and appears to impact rate of autohydrolysis of the D-phosphate; T131 likely involved in coordination of phosphate; K164 likely involved in activating the water molecule that hydrolyzes the acyl intermediate, and/or involved in coordination of oxygen in acyl-phosphate/stabilization of phosphorylated state; D189,D194 likely coordinate Mg or other metal cation. (Mg or other metal cations are not conserved in epoxide hydrolases and dehalogenases, but are conserved and required for the activity of phosphohydrolases/phosphotransferases).

II. High-Throughput in vitro Fluorescence Polarization Assay

Fluorescently-labeled HADH peptide/substrate are added to each well of a 96-well microtiter plate, along with a test agent in a test buffer (10 mM HEPES, 10 mM NaCl, 6 mM magnesium chloride, pH 7.6). Changes in fluorescence polarization, determined by using a Fluorolite FPM-2 Fluorescence Polarization Microtiter System (Dynatech Laboratories, Inc), relative to control values indicates the test compound is a candidate modifier of HADH activity.

III. High-Throughput in vitro Binding Assay $^{33}$P-labeled HADH peptide is added in an assay buffer (100 mM KCl, 20 mM HEPES pH 7.6, 1 mM MgCl$_2$, 1% glycerol, 0.5% NP-40, 50 mM beta-mercaptoethanol, 1 mg/ml BSA, cocktail of protease inhibitors) along with a test agent to the wells of a Neutralite-avidin coated assay plate and incubated at 25° C. for 1 hour. Biotinylated substrate is then added to each well and incubated for 1 hour. Reactions are stopped by washing with PBS, and counted in a scintillation counter. Test agents that cause a difference in activity relative to control without test agent are identified as candidate p21 modulating agents.

IV. Immunoprecipitations and Immunoblotting

For coprecipitation of transfected proteins, 3×10$^6$ appropriate recombinant cells containing the HADH proteins are plated on 10-cm dishes and transfected on the following day with expression constructs. The total amount of DNA is kept constant in each transfection by adding empty vector. After 24 h, cells are collected, washed once with phosphate-buffered saline and lysed for 20 min on ice in 1 ml of lysis buffer containing 50 mM Hepes, pH 7.9, 250 mM NaCl, 20 mM glycerophosphate, 1 mM sodium orthovanadate, 5 mM p-nitrophenyl phosphate, 2 mM dithiothreitol, protease inhibitors (complete, Roche Molecular Biochemicals), and 1% Nonidet P-40. Cellular debris is removed by centrifugation twice at 15,000×g for 15 min. The cell lysate is incubated with 25 µl of M2 beads (Sigma) for 2 h at 4° C. with gentle rocking.

After extensive washing with lysis buffer, proteins bound to the beads are solubilized by boiling in SDS sample buffer, fractionated by SDS-polyacrylamide gel electrophoresis, transferred to polyvinylidene difluoride membrane and blotted with the indicated antibodies. The reactive bands are visualized with horseradish peroxidase coupled to the appropriate secondary antibodies and the enhanced chemiluminescence (ECL) Western blotting detection system (Amersham Pharmacia Biotech).

V. Expression Analysis

All cell lines used in the following experiments are NCI (National Cancer Institute) lines, and are available from ATCC (American Type Culture Collection, Manassas, Va. 20110–2209). Normal and tumor tissues were obtained from Impath, UC Davis, Clontech, Stratagene, and Ambion.

TaqMan analysis was used to assess expression levels of the disclosed genes in various samples.

RNA was extracted from each tissue sample using Qiagen (Valencia, Calif.) RNeasy kits, following manufacturer's protocols, to a final concentration of 50 ng/µl. Single stranded cDNA was then synthesized by reverse transcribing the RNA samples using random hexamers and 500 ng of total RNA per reaction, following protocol 4304965 of Applied Biosystems (Foster City, Calif., website at appliedbiosystems.com).

Primers for expression analysis using TaqMan assay (Applied Biosystems, Foster City, Calif.) were prepared according to the TaqMan protocols, and the following criteria:
a) primer pairs were designed to span introns to eliminate genomic contamination, and
b) each primer pair produced only one product.

Taqman reactions were carried out following manufacturer's protocols, in 25 µl total volume for 96-well plates and 10 µl total volume for 384-well plates, using 300 nM primer and 250 nM probe, and approximately 25 ng of cDNA. The standard curve for result analysis was prepared using a universal pool of human cDNA samples, which is a mixture of cDNAs from a wide variety of tissues so that the chance that a target will be present in appreciable amounts is good. The raw data were normalized using 18S rRNA (universally expressed in all tissues and cells).

For each expression analysis, tumor tissue samples were compared with matched normal tissues from the same patient. A gene was considered overexpressed in a tumor when the level of expression of the gene was 2 fold or higher in the tumor compared with its matched normal sample. In cases where normal tissue was not available, a universal pool of cDNA samples was used instead. In these cases, a gene was considered overexpressed in a tumor sample when the difference of expression levels between a tumor sample and the average of all normal samples from the same tissue type was greater than 2 times the standard deviation of all normal samples (i.e., Tumor-average (all normal samples) >2×STDEV(all normal samples)).

HADH (SEQ ID NO:1) was overexpressed in 10 of 30 matched colon tumors, and 2 of 7 matched ovarian tumors. A modulator identified by an assay described herein can be further validated for therapeutic effect by administration to a tumor in which the gene is overexpressed. A decrease in tumor growth confirms therapeutic utility of the modulator. Prior to treating a patient with the modulator, the likelihood that the patient will respond to treatment can be diagnosed by obtaining a tumor sample from the patient, and assaying for expression of the gene targeted by the modulator. The expression data for the gene(s) can also be used as a diagnostic marker for disease progression. The assay can be performed by expression analysis as described above, by antibody directed to the gene target, or by any other available detection method.

What is claimed is:

1. A method of identifying a candidate HADH modulating agent, said method comprising the steps of:
   (a) providing an assay system comprising a purified or recombinant HADH polypeptide comprising amino acid residues 9 to 212 as set forth in SEQ ID NO:3, or a purified or recombinant HADH nucleic acid encoding said polypeptide;
   (b) contacting the assay system with a test agent under conditions whereby, but for the presence of the test agent, the system provides a reference activity; and
   (c) detecting a test agent-biased activity of the assay system, wherein a difference between the test agent-biased activity and the reference activity identifies the test agent as a candidate HADH modulating agent.

2. The method of claim 1 wherein the assay system comprises cultured cells that express the HADH polypeptide.

3. The method of claim 2 wherein the cultured cells additionally have defective p21 function, wherein the defective p21 function is selected from the group consisting of complete loss of p21 and overexpression of p21.

4. The method of claim 1 wherein the assay system comprises said HADH polypeptide, and the test agent is an organic, non-peptide molecule, having a molecular weight less than 1000.

5. The method of claim 4 wherein the assay is a binding assay.

6. The method of claim 1 wherein the assay system is selected from the group consisting of an apoptosis assay system, a cell proliferation assay system, an angiogenesis assay system, and a hypoxic induction assay system.

7. The method of claim 1 wherein the assay system includes a binding assay comprising said HADH polypeptide and the candidate test agent is an antibody.

8. The method of claim 1 wherein the assay system includes an expression assay comprising said HADH nucleic acid and the candidate test agent is a nucleic acid.

9. The method of claim 8 wherein the nucleic acid is an antisense oligomer.

10. The method of claim 8 wherein the nucleic acid PMO.

11. The method of claim 1 additionally comprising:
    (d) administering the candidate HADH modulating agent identified in (c) to a model system comprising cells defective in p21 function and, detecting a phenotypic change in the model system that indicates that the p21 function is restored, wherein the defective p21 function is selected from the group consisting of complete loss of p21 and overexpression of p21.

12. The method of claim 11 wherein the model system is a mouse.

13. The method of claim 1, comprising the additional steps of:
   (d) providing a secondary assay system comprising cultured cells or a non-human animal expressing HADH, polypeptide comprising amino acid residues 9 to 212 as set forth in SEQ ID NO:3, and wherein the secondary assay system measures p21 function,
   (e) contacting the secondary assay system with a candidate clinical compound under conditions whereby, but for the presence of the candidate clinical compound, the system provides a reference activity indicative of p21 function; and
   (f) detecting a candidate clinical compound-biased activity of the second assay system,
   wherein a difference between the candidate clinical compound-biased activity and the reference activity of the second assay system confirms the candidate clinical compound as a p21 modulating agent, and wherein the second assay detects a candidate clinical compound-biased change in p21.

14. The method of claim 13 wherein the secondary assay system comprises cultured cells.

15. The method of claim 13 wherein the secondary assay system comprises a mouse.

16. The method of claim 15 wherein the mouse is a p21 knockout mouse.

17. The method of claim 1 wherein said HADH polypeptide comprises the amino acid sequence of SEQ ID NO:3.

18. The method of claim 1 wherein said HADH nucleic acid comprises SEQ ID NO:1.

19. The method of claim 12 wherein the mouse is a p21 knockout mouse.

20. The method of claim 12 wherein the mouse overexpresses wild-type p21.

21. The method of claim 15 wherein the mouse overexpresses wild-type p21.

* * * * *

SEQUENCE LISTING

<160> NUMBER OF SEQ ID NOS: 4

<210> SEQ ID NO 1
<211> LENGTH: 2352
<212> TYPE: DNA
<213> ORGANISM: Homo sapiens

<400> SEQUENCE: 1

```
aggctacggt tcgcgccagc ggccggcgct atggggctga gccgcgtgcg ggcggttttc      60
tttgacttgg acaacactct catcgacacg gccggggcga gcaggagagg catgttggag     120
gtgataaaac tcttacaatc aaaataccat tataaagaag aggctgaaat catctgtgat     180
aaagttcaag ttaaactcag caaggaatgt tttcatcctt acaatacatg cattactgat     240
ttaaggactt cacattggga agaagcaatc caggaaacaa aaggtggtgc agccaataga     300
aaattggctg aagaatgtta tttcctttgg aaatctacac gtttacagca tatgacacta     360
gcagaagacg tcaaagccat gcttactgaa cttcgaaagg aggtccgcct acttctatta     420
acgaatgggg acagacagac ccagagggag aagattgagg cttgtgcctg tcagtcctat     480
tttgacgctg ttgttgtagg tggagagcag agagaggaga aaccagcacc gtccatattt     540
```

| | |
|---|---|
| tattactgct gcaatcttct cggagtacaa cctgggggact gtgtgatggt cggtgacaca | 600 |
| ttagaaaccg acatccaagg aggcctcaat gcaggattga agcaacagt ctggatcaat | 660 |
| aaaaatggaa tagtgccact gaagtcctcc ccagttccgc attacatggt ttcttctgtg | 720 |
| ctagagttac ctgctctctt acaaagtata gactgcaaag tcagtatgtc cacttaaagc | 780 |
| acataaaagg gcatgattat gaatgttaga atcaatttgc tgagtatgaa ataagaaaag | 840 |
| ttagggcact ccactttatga taatccagct ctaagaataa ttttacttat gatttaatgg | 900 |
| ccaatatttt gaaggtcttc ccaaccctat tgcttctaag ttgtaacaac caaccattga | 960 |
| gtggtactta tatctgaaaa ttcagattgc atgaattcag gtcagtagta tagcccagaa | 1020 |
| aatttaagga aatatattat ttgttagtct gtatctggag cttttttaaaa ttatgttatt | 1080 |
| aatcttttag tatcttggct gcataatgcc aagcaggatt gctttacaca tggatgcaca | 1140 |
| aatgtaaggt ttatcttctg gcttaaaaat agatatttt aaaaaataga ttttctaaaa | 1200 |
| cacagattta tgaaagcaag tgaatctggt taatatgaaa taagtactaa gtcacatgca | 1260 |
| aatcaaggta ttatatagtg aaattatttt gcatattttg aaaacataaa ccatagtttt | 1320 |
| tgcctacttt ggatgtatac tttcttttat gaacctgatt tttctgtatg acattttttt | 1380 |
| tttttttcaga gggcagggag caattttttct atggcatgtg acagattcct ccagttagaa | 1440 |
| aaagctgtta aaatcaacac atggtgctct tttaccgtga cattttctca cctgtgcaca | 1500 |
| gtgagccgat agcttccttt tagtcttcac ctctcaagga aatgttttta ctgtcttttc | 1560 |
| ccagacacac agtgggggttg agggagctag gctgttttgc tagagataat tgcaaggcac | 1620 |
| gtggcactaa aagtcatttt tcttctgtgg atccataaga ggaacatttc ctcagtgtag | 1680 |
| cctaacaatg cagcccccaa tctgttcctt ttttttttg aaatgggatc tctgtcgccc | 1740 |
| aggttggagt gccatggcac catctcggct cactgcaacc tctgcctcct gagctcaagt | 1800 |
| gatcctccca cctcagcctc ccaagggtgt gtgtgactac aagtacacac taccacgccc | 1860 |
| agctaatgtg ttttttttgta gagatgggat tttgccatgt tgcccaggct ggtctcgaat | 1920 |
| tcctggattc aagtgatcct cccacctcag cctcctaaag tcctaggatt ataggcatga | 1980 |
| gccactgtgc ctggccctct catctgatag aaaattagat tttgctatga gccatttcct | 2040 |
| gagggccaat ttaatactcg tgtgactctt cttagagtta ccatctgcct taaatttcct | 2100 |
| ctgttttttca cattcttgga aatatatcat tgttttgcaa atttctatat ctaattcagg | 2160 |
| gtttaccagg agcttaataa ttaatggcta catagcaagg catcgtcttg gaaccggaga | 2220 |
| atttttctcta gactattagg ctagacagtc tcatgattat actaaccaaa cctggagtaa | 2280 |
| agtggttgaa aaaaaagaaa gtataaaggg gcttattaaa gtggttaata aatatgaaaa | 2340 |
| aaaaaaaaaa aa | 2352 |

<210> SEQ ID NO 2
<211> LENGTH: 892
<212> TYPE: DNA
<213> ORGANISM: Homo sapiens

<400> SEQUENCE: 2

| | |
|---|---|
| ccacgcgtcc ggccggcgct atggggctga gccgcgtgcg ggcggttttc tttgacttgg | 60 |
| acaacactct catcgacacg gccggggcga gcaggagagg catgttggag gtgataaaac | 120 |
| tcttacaatc aaaataccat tataaagaag aggctgaaat catctgtgat aaagttcaag | 180 |
| ttaaactcag caaggaatgt tttcatcctt acaatacatg cattactgat ttaaggactt | 240 |
| cacattggga agaagcaatc caggaaacaa aaggtggtgc agccaataga aaattggctg | 300 |

```
aagaatgtta tttcctttgg aaatctacac gtttacagca tatgacacta gcagaagacg    360
tcaaagccat gcttactgaa cttcgaaagg aggtccgcct acttctatta acgaatgggg    420
acagacagac ccagagggag aagattgagg cttgtgcctg tcagtcctat tttgacgctg    480
ttgttgtagg tggagagcag agagaggaga accagcacc gtccatattt tattactgct    540
gcaatcttct cggagtacaa cctggggact gtgtgatggt cggtgacaca ttagaaaccg    600
acatccaagg aggcctcaat gcaggattga agcaacagt ctggatcaat aaaaatggaa    660
tagtgccact gaagttctcc ccagttccgc attacatggc ttcttctgtg ctagagttac    720
ctgctctctt acaaagcata gactgcaaag tcagtatgtc cacttaaagc acataacaag    780
ggcatgatta tgaatgttaa aatcaatttt gcctgagtat gcaatacaaa agttagggc    840 actccccttt atgataatcc agcttctaag aatcattttc acttaatgat tt            892
```

<210> SEQ ID NO 3
<211> LENGTH: 212
<212> TYPE: PRT
<213> ORGANISM: Homo sapiens

<400> SEQUENCE: 3

```
Ala Gly Ala Met Gly Leu Ser Arg Val Arg Ala Val Phe Phe Asp Leu
1               5                   10                  15

Asp Asn Thr Leu Ile Asp Thr Ala Gly Ala Ser Arg Arg Gly Met Leu
                20                  25                  30

Glu Val Ile Lys Leu Leu Gln Ser Lys Tyr His Tyr Lys Glu Glu Ala
            35                  40                  45

Glu Ile Ile Cys Asp Lys Val Gln Val Lys Leu Ser Lys Glu Cys Phe
        50                  55                  60

His Pro Tyr Asn Thr Cys Ile Thr Asp Leu Arg Thr Ser His Trp Glu
65                  70                  75                  80

Glu Ala Ile Gln Glu Thr Lys Gly Gly Ala Ala Asn Arg Lys Leu Ala
                85                  90                  95

Glu Glu Cys Tyr Phe Leu Trp Lys Ser Thr Arg Leu Gln His Met Thr
            100                 105                 110

Leu Ala Glu Asp Val Lys Ala Met Leu Thr Glu Leu Arg Lys Glu Val
        115                 120                 125

Arg Leu Leu Leu Leu Thr Asn Gly Asp Arg Gln Thr Gln Arg Glu Lys
    130                 135                 140

Ile Glu Ala Cys Ala Cys Gln Ser Tyr Phe Asp Ala Val Val Val Gly
145                 150                 155                 160

Gly Glu Gln Arg Glu Glu Lys Pro Ala Pro Ser Ile Phe Tyr Tyr Cys
                165                 170                 175

Cys Asn Leu Leu Gly Val Gln Pro Gly Asp Cys Val Met Val Gly Asp
            180                 185                 190

Thr Leu Glu Thr Asp Ile Gln Gly Gly Leu Asn Ala Gly Leu Lys Ala
        195                 200                 205

Thr Val Trp Ile
    210
```

<210> SEQ ID NO 4
<211> LENGTH: 248
<212> TYPE: PRT
<213> ORGANISM: Homo sapiens

<400> SEQUENCE: 4

-continued

```
Met Gly Leu Ser Arg Val Arg Ala Val Phe Phe Asp Leu Asp Asn Thr
 1               5                  10                  15

Leu Ile Asp Thr Ala Gly Ala Ser Arg Arg Gly Met Leu Glu Val Ile
             20                  25                  30

Lys Leu Leu Gln Ser Lys Tyr His Tyr Lys Glu Glu Ala Glu Ile Ile
             35                  40                  45

Cys Asp Lys Val Gln Val Lys Leu Ser Lys Glu Cys Phe His Pro Tyr
             50                  55                  60

Asn Thr Cys Ile Thr Asp Leu Arg Thr Ser His Trp Glu Glu Ala Ile
 65                  70                  75                  80

Gln Glu Thr Lys Gly Gly Ala Ala Asn Arg Lys Leu Ala Glu Glu Cys
             85                  90                  95

Tyr Phe Leu Trp Lys Ser Thr Arg Leu Gln His Met Thr Leu Ala Glu
             100                 105                 110

Asp Val Lys Ala Met Leu Thr Glu Leu Arg Lys Glu Val Arg Leu Leu
             115                 120                 125

Leu Leu Thr Asn Gly Asp Arg Gln Thr Gln Arg Glu Lys Ile Glu Ala
     130                 135                 140

Cys Ala Cys Gln Ser Tyr Phe Asp Ala Val Val Val Gly Gly Glu Gln
145                 150                 155                 160

Arg Glu Glu Lys Pro Ala Pro Ser Ile Phe Tyr Tyr Cys Cys Asn Leu
             165                 170                 175

Leu Gly Val Gln Pro Gly Asp Cys Val Met Val Gly Asp Thr Leu Glu
             180                 185                 190

Thr Asp Ile Gln Gly Gly Leu Asn Ala Gly Leu Lys Ala Thr Val Trp
     195                 200                 205

Ile Asn Lys Asn Gly Ile Val Pro Leu Lys Ser Ser Pro Val Pro His
     210                 215                 220

Tyr Met Val Ser Ser Val Leu Glu Leu Pro Ala Leu Leu Gln Ser Ile
225                 230                 235                 240

Asp Cys Lys Val Ser Met Ser Thr
             245
```